(12) United States Patent
Nam et al.

(10) Patent No.: US 8,895,602 B1
(45) Date of Patent: Nov. 25, 2014

(54) 6-PYRAZOLYLAMIDO-3-SUBSTITUTED AZABICYCLO[3.1.0]HEXANE COMPOUNDS AS CALCIUM CHANNEL INHIBITORS

(71) Applicant: Korea Institute of Science and Technology, Seoul (KR)

(72) Inventors: Ghil Soo Nam, Seoul (KR); Kyung Il Choi, Seoul (KR); Ae Nim Pae, Seoul (KR); Seon Hee Seo, Seoul (KR); Hyun Ah Choo, Seoul (KR); Gyo Chang Keum, Seoul (KR); Jung Hyun Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 14/013,487

(22) Filed: Aug. 29, 2013

(30) Foreign Application Priority Data

May 15, 2013 (KR) .................. 10-2013-0054919

(51) Int. Cl.
*A61K 31/4155* (2006.01)
*C07D 403/12* (2006.01)

(52) U.S. Cl.
CPC .......... *C07D 403/12* (2013.01); *A61K 31/4155* (2013.01)
USPC ......... 514/406; 514/407; 514/414; 548/364.7

(58) Field of Classification Search
None
See application file for complete search history.

(56) References Cited

FOREIGN PATENT DOCUMENTS

WO    WO2009090548    *   7/2009

OTHER PUBLICATIONS

Shafer, S., Kolkhof, P. Failure is an option: learning from unsuccessful proof-of-concept trials. Drug Discovery Today. Nov. 2008, 13, 913-916.*

Horig, H., Pullman, W. From bench to clinic and back: Perspective on the 1st IQPC Translational Research conference. Journal of Translational Medicine. Dec. 2004, 2, 44.*
Chemical Abstract Registry No. 1369236-41-8, indexed in the Registry File on STN CAS Online Apr. 16, 2012.*
Chemical Abstract Registry No. 929107-10-8, indexed in the Registry File on STN CAS Online Apr. 4, 2007.*
Chemical Abstract Registry No. 1156161-66-8, indexed in the Registry File on STN CAS Online Jun. 12, 2009.*
Khosravani, Houman et al., "Effects of $Ca_v3.2$ Channel Mutations Linked to Idiopathic Generalized Epilepsy", *Annals of Neurology*, vol. 57, No. 7, May 2005, pp. 745-749.
Vitko, Iuliia et al., "Functional Characterization and Neuronal Modeling of the Effects of Childhood Absence Epilepsy Variants of CACNA1H, a T-Type Calcium Channel", *The Journal of Neuroscience*, vol. 25, No. 19, May 11, 2005, pp. 4844-4855.
Clozel, Jean Paul et al., "The Structurally Novel $Ca^{2+}$Channel Blocker Ro 40-5967, Which Binds to the [$^3$H] Desmethoxyverapamil Receptor, Is Devoid of the Negative Inotropic Effects of Verapamil in Normal and Failing Rat Hearts", *Cardiovascular Drugs and Therapy*, vol. 4, 1990, pp. 731-736.
Hefti, F. et al., "Antihypertensive Properties of the Novel Calcium Antagonist (1S,2S)-2[2-[[3-(2-Benzimidazolyl)propyl]methylamino]ethyl]-6-fluro-1,2,3,4-tetrahydro-1-isopropyl-2-naphthyl Methoxyacetate Dihydrochloride in Rat Models of Hypertension", *Arzneimittel-Forschung/Drug Research*, vol. 40, 1990, pp. 417-421.
Moosmang, Sven et al., "Antihypertensive Effects of the Putative T-Type Calcium Channel Antagonist Mibefradil Are Mediated by the L-Type Calcium Channel $Ca_v1.2$", Circulation Research, vol. 98, No. 1, 2006, pp. 105-110.
Santoni, Giorgio et al., "Functional role of T-type calcium channel in tumour growth and progression: prospective in cancer therapy" British Journal of Pharmacology, vol. 166, 2012, pp. 1244-1246.
Dogrul, Ahmet et al., "Reversal of experimental neuropathic pain by T-type calcium channel blockers", *Pain*, vol. 105, 2003, pp. 159-168.

\* cited by examiner

*Primary Examiner* — Michael Barker
*Assistant Examiner* — Po-Chih Chen
(74) *Attorney, Agent, or Firm* — Staas & Halsey LLP

(57) ABSTRACT

The present invention relates to a 6-pyrazolylamido-3-substituted azabicyclo[3.1.0]hexane derivatives useful as calcium channel blockers, pharmaceutically acceptable salts thereof and medical use of the calcium channel inhibiting effect of the compounds for treatment of diseases.

7 Claims, 1 Drawing Sheet

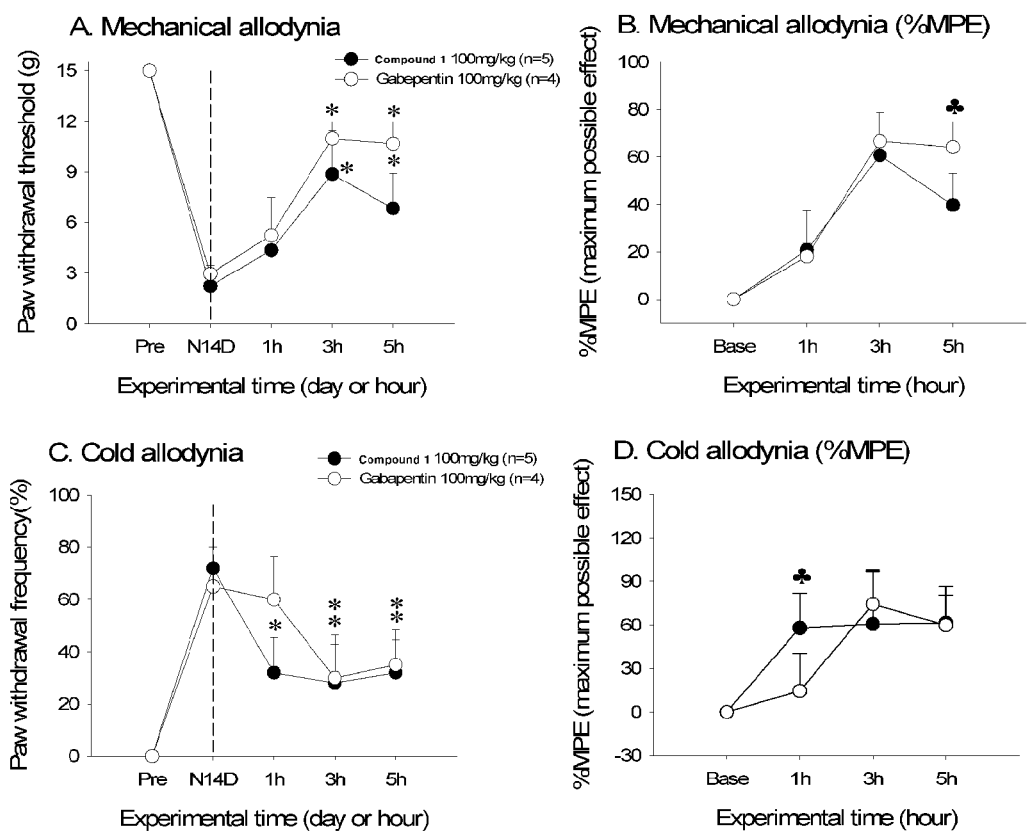

6-PYRAZOLYLAMIDO-3-SUBSTITUTED AZABICYCLO[3.1.0]HEXANE COMPOUNDS AS CALCIUM CHANNEL INHIBITORS

CROSS-REFERENCE TO RELATED APPLICATIONS

This application claims priority under 35 U.S.C. §119 to Korean Patent Application No. 10-2013-0054919, filed on May 15, 2013, in the Korean Intellectual Property Office, the disclosure of which is incorporated herein by reference in its entirety.

BACKGROUND (a) Technical Field

The present invention relates to 6-pyrazolylamido-3-substituted azabicyclo[3.1.0]hexane derivatives useful as calcium channel inhibitors, pharmaceutically acceptable salts thereof and a medical use of the calcium channel inhibiting effect of the compounds for treatment of diseases.

(b) Background Art

Voltage-gated calcium channels play important roles in various intracellular signal transductions by increasing the concentration of calcium ions in response to stimuli to neurons. The calcium channels are divided into high-voltage activated calcium channels and low-voltage activated calcium channels. A representative low-voltage activated calcium channel is the T-type calcium channel.

The T-type calcium channels are found in the central nervous system, adrenal glands, sinoatrial node of the heart, or the like. T-type calcium channel blockers are known to be effective in treatment of cerebral diseases and cardiac diseases such as epilepsy, hypertension, angina, etc. [1) Hosravani, Houman et al., "Effects of Cav3.2 channel mutations linked to idiopathic generalized epilepsy", Annals of Neurology (2005), 57 (5), 745-749; 2) Vitko, Iuliia et al., "Functional characterization and neuronal modeling of the effects of childhood absence epilepsy variants of CACNA1H, a T-type calcium channel", Journal of Neuroscience (2005), 25 (19), 4844-4855; 3) Clozel, Cardiovas Drugs Ther. (1990), 4, pp. 731-736; 4) Hefti, Arzneimittelforschung (1990), 40, 417-421; 5) Moosmang, Sven et al., "Antihypertensive Effects of the Putative T-Type Calcium Channel Antagonist Mibefradil Are Mediated by the L-Type Calcium Channel Cav1.2", Circulation Research (2006), 98 (1), 105-110].

It is also reported that the T-type calcium channels are involved in the proliferation of cancer cells and T-type calcium channel blockers are effective anticancer agents that inhibit the proliferation of cancer cells [Functional role of T-type calcium channel in tumor growth and progression: prospective in cancer therapy" British Journal of Pharmacology, (2012), 166, 1244-1246]

Recent reports have revealed that T-type calcium channel blockers have therapeutic effects on pain. For example, the T-type calcium channel blockers mibefradil and ethosuximide were shown to inhibit mechanically and thermally induced pain in a dose-dependent manner in a spinal nerve ligation model, indicating that T-type calcium channel blockers are useful in the treatment of neuropathic pain [Dogrul, Ahmet et al., "Reversal of experimental neuropathic pain by T-type calcium channel blockers", Pain, 2003, 105, 159-168].

Some drugs having calcium channel inhibition activity have been approved as pharmaceutical drugs. Gabapentin (Neurontin™) and ziconotide (Prialt™) were approved by the FDA as anticonvulsant and for treatment of neuropathic pain but there are problems of limited application depending on patients and tranquilizing effect caused by overdosage. Especially the T-type calcium channel inhibitor Mibefradil (Ro 40-5967, WO 98/49149) had been used to treat hypertension and angina. However, it is metabolized by cytochrome P-450 3A4 and 2D6 and interacts with other drugs pharmacokinetically, thereby resulting in various side effects. As a result, mibefradil has been withdrawn from the market and there is no drug that can be used as a T-type calcium channel blocker. Accordingly, development of a new T-type calcium channel blocker is urgently needed.

The inventors of the present invention have made efforts to develop novel compounds that act on calcium channels. As a result, they have found out that 6-pyrazolylamido-3-substituted azabicyclo[3.1.0]hexane derivatives synthesized as novel compounds have superior antagonistic activity against T-type calcium channels.

SUMMARY

The present invention provides 6-pyrazolylamido-3-substituted azabicyclo[3.1.0]hexane derivatives of novel structure having various substituents and pharmaceutically acceptable salts thereof.

The present invention also provides a pharmaceutical composition for treating and preventing cerebral diseases, cardiac diseases, cancers or pain-related diseases by effectively blocking T-type calcium channels, which contains a 6-pyrazolylamido-3-substituted azabicyclo[3.1.0]hexane derivative or a pharmaceutically acceptable salt thereof as an active ingredient. More specifically, the novel compound of the present invention is useful for treating and preventing cerebral diseases such as epilepsy, depression, dementia, sleep disorder, diabetes, obesity, etc., cardiac diseases such as hypertension, cardiac dysrhythmia, angina, myocardial infarction, congestive heart failure, etc., cancers such as liver cancer, lung cancer, colon cancer, prostate cancer, breast cancer, uterine cancer, esophageal cancer, brain cancer, etc. and pain-related diseases such as chronic and acute pain, neuropathic pain, etc.

The present invention further provides a method for preparing 6-pyrazolylamido-3-substituted azabicyclo[3.1.0] hexane derivatives.

The present invention still further provides a novel intermediate compounds obtained during the preparation of 6-pyrazolylamido-3-substituted azabicyclo[3.1.0]hexane derivatives.

In an aspect, the present invention provides a 6-pyrazolylamido-3-substituted azabicyclo[3.1.0]hexane derivative represented by Formula 1 and a pharmaceutically acceptable salt thereof, which exhibits selective antagonistic activity against the T-type calcium channel and thus is useful for treating and preventing cerebral diseases, cardiac diseases, cancers or pain-related diseases:

[Formula 1]

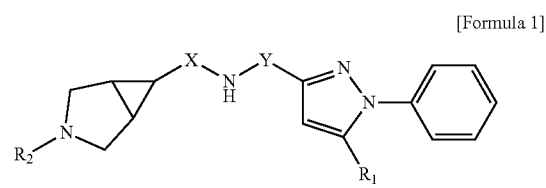

wherein

—X—NH—Y— represents —C(O)NH(CH$_2$)$_q$ or —(CH$_2$)$_q$NHC(O)—;

$R_1$ represents $C_1$-$C_6$ alkyl;
$R_2$ represents $C_1$-$C_6$ alkyl,

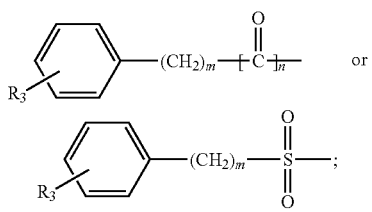

$R_3$ represents hydrogen, $C_1$-$C_6$ alkyl or $C_1$-$C_6$ haloalkyl substituted with 1-6 halogen atom(s); and each of q, m and n represents an integer from 0 to 6.

The novel compound of the present invention exhibits effective activity as a T-type calcium channel inhibitor.

Accordingly, the novel compound of the present invention is useful for treating and preventing cerebral diseases, cardiac diseases, cancers or pain-related diseases by effectively blocking the T-type calcium channel. More specifically, the novel compound of the present invention is useful for treating and preventing cerebral diseases such as epilepsy, depression, dementia, sleep disorder, diabetes, obesity, etc., cardiac diseases such as hypertension, cardiac dysrhythmia, angina, myocardial infarction, congestive heart failure, etc., cancers such as liver cancer, lung cancer, colon cancer, prostate cancer, breast cancer, uterine cancer, esophageal cancer, brain cancer, etc. and pain-related diseases such as chronic and acute pain, neuropathic pain, etc.

Other features and aspects of the present invention will be apparent from the following detailed description, drawing and claims.

BRIEF DESCRIPTION OF THE DRAWING

The above and other objects, features and advantages of the present invention will now be described in detail with reference to certain exemplary embodiments thereof illustrated in the accompanying drawing which is given hereinbelow by way of illustration only, and thus are not limitative of the invention, and wherein:

FIG. 1 compares the therapeutic effect of Compound 1 of the present invention and gabapentin for mechanical allodynia and cold allodynia.

In FIG. 1, A and C show paw withdrawal threshold (PWT) and B and D show maximum possible effect (% MPE).

*$P<0.05$ (gabapentin), *$P<0.05$ (Compound 1) vs. pre-administration value (paired t-test).

♣ $P<0.05$ gabapentin vs. Compound 1 (unpaired t-test).

DETAILED DESCRIPTION

Hereinafter, reference will now be made in detail to various embodiments of the present invention, examples of which are illustrated in the accompanying drawing and described below. While the invention will be described in conjunction with exemplary embodiments, it will be understood that the present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The 6-pyrazolylamido-3-substituted azabicyclo[3.1.0] hexane derivatives represented by Formula 1 according to the present invention may have chiral centers and, in that case, there may exist racemic compounds or all possible isomers. Accordingly, the present invention includes those racemates, isomers or isomeric mixtures.

The present invention also includes radioactive derivatives of the 6-pyrazolylamido-3-substituted azabicyclo[3.1.0]hexane derivatives represented by Formula 1. These radioactive compounds are useful in biomedical researches.

Pharmaceutically acceptable salts of the 6-pyrazolylamido-3-substituted azabicyclo[3.1.0]hexane derivatives represented by Formula 1 according to the present invention may be formed by methods commonly employed in the art. For example, pharmaceutically acceptable acid salts may be formed with nontoxic inorganic acids such as hydrochloric acid, bromic acid, sulfonic acid, amidosulfuric acid, phosphoric acid and nitric acid or nontoxic organic acids such as propionic acid, succinic acid, glycolic acid, stearic acid, lactic acid, tartaric acid, citric acid, p-toluenesulfonic acid and methanesulfonic acid.

The substituents of the 6-pyrazolylamido-3-substituted azabicyclo[3.1.0]hexane derivative represented by Formula 1 according to the present invention will be described in further detail. 'Alkyl' includes any linear, branched or cyclic carbon chain containing 1-6 carbon atoms. Preferred alkyl groups include methyl, ethyl, propyl, isopropyl, butyl, isobutyl, tert-butyl, neopentyl, cyclopentyl, cyclohexyl, etc. 'Haloalkyl' refers to an alkyl group substituted with 1-6 halogen atom(s). Preferred haloalkyl groups include chloromethyl, dichloromethyl, trifluoromethyl, fluoroethyl, tetrafluoroethyl, etc.

Specifically, in the 6-pyrazolylamido-3-substituted azabicyclo[3.1.0]hexane derivative represented by Formula 1 according to the present invention, —X—NH—Y— may represent —C(O)NH(CH$_2$)— or —(CH$_2$)NHC(O)—, $R_1$ may represent isobutyl and $R_2$ may represent methyl, isopropyl, 3-methylbutyl, 3,3-dimethylbutyl, phenyl, 4-(trifluoromethyl)phenyl, benzyl, 4-(trifluoromethyl)benzyl, phenylethyl, 4-(trifluoromethyl)phenylethyl, benzoyl, 2-phenylacetyl, benzenesulfonyl, benzylsulfonyl or phenylethylsulfonyl.

Specific examples of the 6-pyrazolylamido-3-substituted azabicyclo[3.1.0]hexane derivative represented by Formula 1 according to the present invention include:
3-[3-(3,3-dimethylbutyl)-3-azabicyclo[3.1.0]hexane-6-carboxamido]methyl-5-isobutyl-1-phenyl-1H-pyrazole (Compound 1);
3-(3-benzyl-3-azabicyclo[3.1.0]hexane-6-carboxamido)methyl-5-isobutyl-1-phenyl-1H-pyrazole (Compound 2);
5-isobutyl-1-phenyl-3-{3-[4-(trifluoromethyl)phenylethyl]-3-azabicyclo[3.1.0]hexane-6-carboxamido}methyl-1H-pyrazole (Compound 3);
3-(3-benzoyl-3-azabicyclo[3.1.0]hexane-6-carboxamido) methyl-5-isobutyl-1-phenyl-1H-pyrazole (Compound 4);
5-isobutyl-1-phenyl-3-[3-(2-phenylacetyl)-3-azabicyclo [3.1.0]hexane-6-carboxamido]methyl-1H-pyrazole (Compound 5);
5-isobutyl-1-phenyl-3-(3-benzenesulfonyl-3-azabicyclo [3.1.0]hexane-6-carboxamido)methyl-1H-pyrazole (Compound 6); and
3-{2-[3-(3,3-dimethylbutyl)-3-azabicyclo[3.1.0]hexane-6-yl]methyl}carbamoyl-5-isobutyl-1-phenyl-1H-pyrazole (Compound 7).

The present invention also includes a method for preparing the 6-pyrazolylamido-3-substituted azabicyclo[3.1.0]hexane derivative represented by Formula 1.

Schemes 1, 2 and 3 are specific examples of methods for introducing various substituents $R_2$ to the compound represented by Formula 1.

According to Scheme 1, a 6-pyrazolylamido-3-substituted azabicyclo[3.1.0]hexane derivative represented by Formula 1a having an $R^a$—$CH_2$— group introduced may be prepared by reacting a pyrazole-azabicyclo[3.1.0]hexane compound represented by Formula 2 with an aldehyde compound represented by Formula 3 by reductive amination.

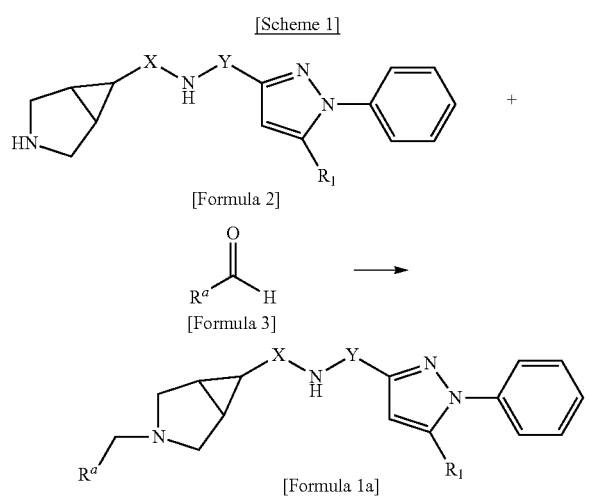

In Scheme 1, $R^a$ represents hydrogen, $C_1$-$C_5$ alkyl or

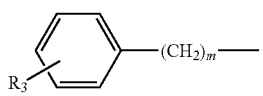

and —X—NH—Y—, $R_1$, $R_3$ and m are the same as defined above.

According to Scheme 2, a 6-pyrazolylamido-3-substituted azabicyclo[3.1.0]hexane derivative represented by Formula 1b having an $R^b$—C(O)— group introduced may be prepared by reacting a pyrazole-azabicyclo[3.1.0]hexane compound represented by Formula 2 with an acyl halide compound represented by Formula 4.

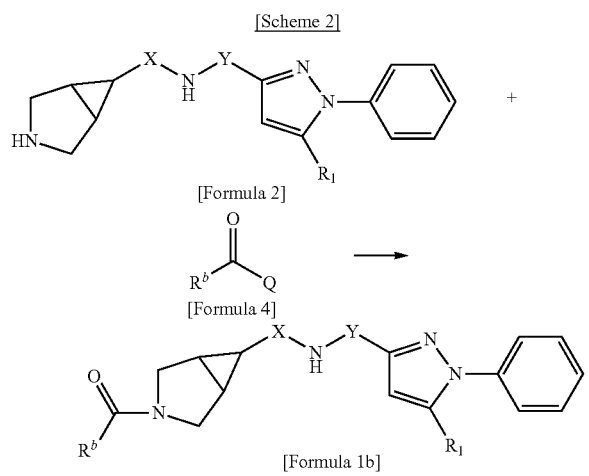

In Scheme 2, $R^b$ represents

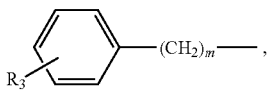

Q represents a halogen atom and —X—NH—Y—, $R_1$, $R_3$ and m are the same as defined above.

According to Scheme 3, a 6-pyrazolylamido-3-substituted azabicyclo[3.1.0]hexane derivative represented by Formula 1c having an $R^b$—$SO_2$— group introduced may be prepared by reacting a pyrazole-azabicyclo[3.1.0]hexane compound represented by Formula 2 with a sulfonyl halide compound prepared by Formula 5.

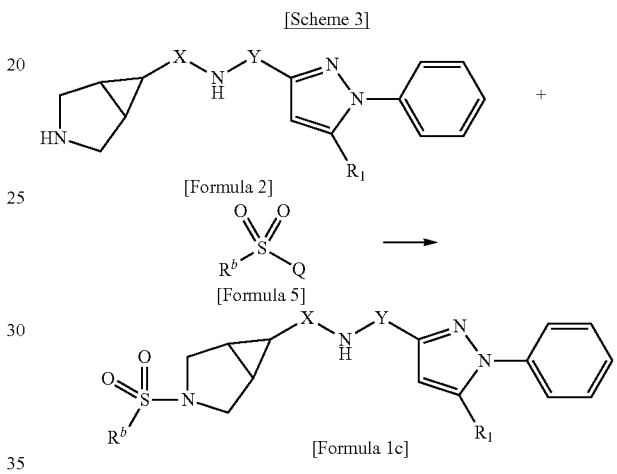

In Scheme 3, $R^b$ represents

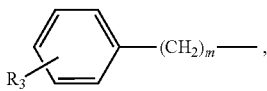

Q represents a halogen atom and —X—NH—Y—, $R_1$, $R_3$ and m are the same as defined above.

The reactions according to Schemes 1-3 may be conducted using an appropriate base and an organic solvent. The base may be an inorganic base such as carbonate, sulfate, hydroxide, etc. of an alkali metal or an alkaline earth metal or an organic base such as mono($C_1$-$C_5$ alkyl)amine, di($C_1$-$C_5$ alkyl)amine, etc. The solvent may be an inert organic solvent commonly used in the art, which does not affect the reactions. Specific examples of the organic solvent that can be used in the present invention include diethyl ether, $C_1$-$C_6$ lower alcohols such as methanol, ethanol or propanol, tetrahydrofuran, halogenated compounds such as chloroform, methylene chloride, etc. and nitrile compounds such as acetonitrile, etc. The reaction may be conducted in a temperature range from 0° C. to the reflux temperature of the used solvent, specifically from room temperature to 100° C., more specifically from 30 to 60° C.

Schemes 4 and 5 show specific examples wherein the —X—NH—Y— in the compound represented by Formula 1 is —$(CH_2)_q$NHC(O)— or —C(O)NH$(CH_2)_q$—.

According to Scheme 4, a 6-pyrazolylamido-3-substituted azabicyclo[3.1.0]hexane derivative represented by Formula 1d having a —$(CH_2)_1$NHC(O)— bond may be prepared by reacting an azabicyclo[3.1.0]hexanamine compound represented by Formula 6 with a pyrazolic acid compound represented by Formula 7.

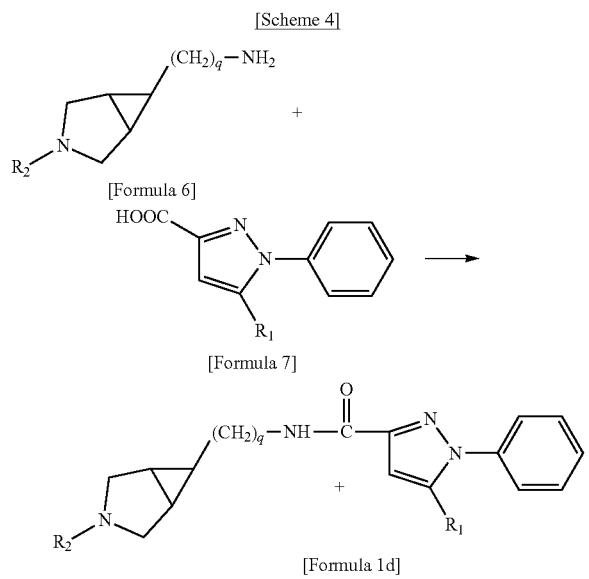

In Scheme 4, $R_1$, $R_2$, and q are the same as defined above.

According to Scheme 5, a 6-pyrazolylamido-3-substituted azabicyclo[3.1.0]hexane derivative represented by Formula 1e having a —C(O)NH(CH$_2$)$_q$— bond may be prepared by reacting an azabicyclo[3.1.0]hexanoic acid compound represented by Formula 8 with pyrazole amine compound represented by Formula 9.

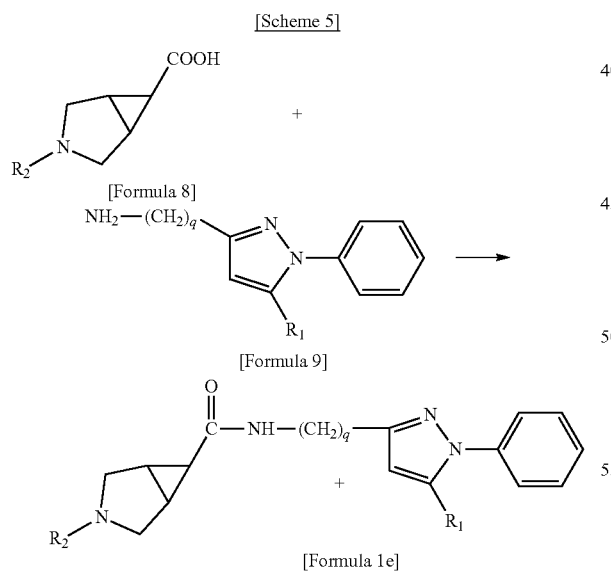

In Scheme 5, $R_1$, $R_2$, and q are the same as defined above.

The coupling reactions according to Schemes 4 and 5 may be conducted using an appropriate coupling agent and an organic solvent. The coupling agent may be a carbodiimide-based coupling agent. Specifically, 1-ethyl-3-(3-dimethylaminopropyl)carbodiimide (EDC), N,N-dicyclohexylcarbodiimide, etc., may be used. The solvent may be an inert organic solvent commonly used in the art, which does not affect the reactions. Specific examples of the organic solvent that can be used in the present invention include diethyl ether, $C_1$-$C_6$ lower alcohols such as methanol, ethanol or propanol, tetrahydrofuran, halogenated compounds such as chloroform, methylene chloride, etc. and nitrile compounds such as acetonitrile, etc. The reaction may be conducted in a temperature range from 0° C. to the reflux temperature of the used solvent, specifically from room temperature to 100° C., more specifically from 30 to 60° C.

The pyrazole-azabicyclo[3.1.0]hexane compound represented by Formula 2 used as starting materials in Schemes 1-3 or an acid salt compound thereof is a novel compound. The acid salt compound may be formed from the compound represented by Formula 2 by reaction with a common organic acid or inorganic acid and may include specifically hydrochloride, sulfate, acetate, etc. Accordingly, the compound represented by Formula 2 or an acid salt compound as a novel intermediate compound is included in the scope of the present invention.

According to Scheme 6, a pyrazole-azabicyclo[3.1.0]hexane compound represented by Formula 2a wherein the —X—NH—Y— in the compound represented by Formula 2 is a —C(O)NH(CH$_2$)$_q$— bond may be prepared. Specifically, it may be prepared by: 1) converting a pyrrole compound represented by Formula 10 to an azabicyclo[3.1.0]hexane ester compound represented by Formula 11; 2) converting the azabicyclo[3.1.0]hexane ester compound represented by Formula 11 to an azabicyclo[3.1.0]hexanoic acid compound represented by Formula 12; 3) converting the azabicyclo[3.1.0] hexanoic acid compound represented by Formula 12 to a tert-butyl pyrazole-azabicyclo[3.1.0]hexane-3-carboxylate compound represented by Formula 13; and 4) converting the tert-butyl pyrazole-azabicyclo[3.1.0]hexane-3-carboxylate compound represented by Formula 13 to the pyrazole-azabicyclo[3.1.0]hexane compound represented by Formula 2a.

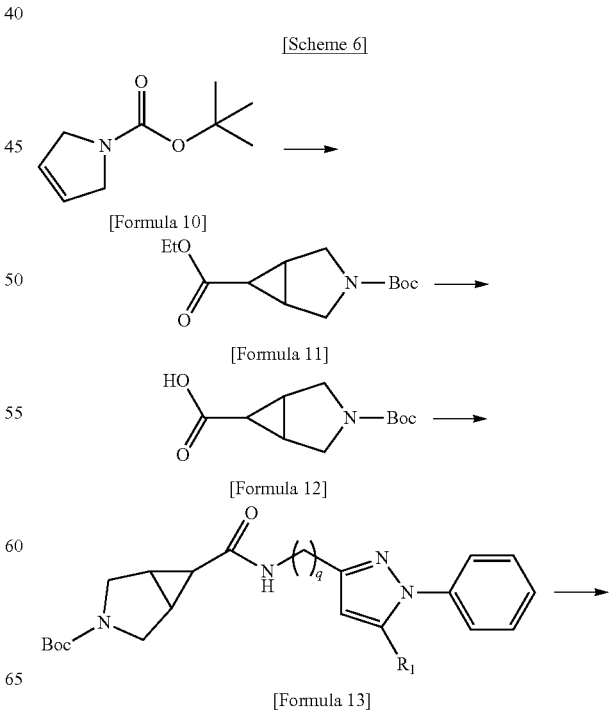

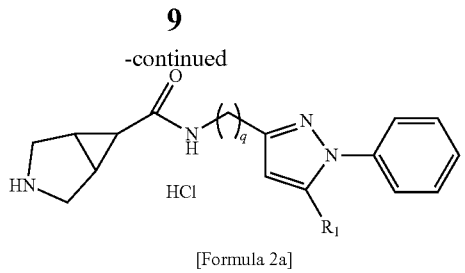

[Formula 2a]

In Scheme 6, $R_1$ and q are the same as defined above.

The method for preparing the pyrazole-azabicyclo[3.1.0]hexane compound represented by Formula 2a according to Scheme 6 will be described in further detail.

The conversion to the azabicyclo[3.1.0]hexane ester compound represented by Formula 11 is achieved by reacting the pyrrole compound represented by Formula 10, which is obtained by introducing the Boc protecting group to pyrroline, with ethyl diazoate in the presence of the rhodium(II) acetate catalyst.

And, the conversion to the azabicyclo[3.1.0]hexanoic acid compound represented by Formula 12 is achieved by hydrolyzing the azabicyclo[3.1.0]hexane ester compound represented by Formula 11. The hydrolysis may be conducted under a usually employed acidic or basic condition, specifically using sodium hydroxide as a base.

And, the conversion to the tert-butyl pyrazole-azabicyclo[3.1.0]hexane-3-carboxylate compound represented by Formula 13 is achieved by reacting the azabicyclo[3.1.0]hexanoic acid compound represented by Formula 12 with a pyrazole amine compound represented by Formula 9 by amide coupling.

And, the conversion to the pyrazole-azabicyclo[3.1.0]hexane compound represented by Formula 2a is achieved by removing the Boc protecting group from the tert-butyl pyrazole-azabicyclo[3.1.0]hexane-3-carboxylate compound represented by Formula 13.

In the preparation method according to Scheme 6, an inert organic solvent commonly used in the art, which does not affect the reactions, may be used as a reaction solvent. Specific examples of the organic solvent that can be used in the present invention include diethyl ether, $C_1$-$C_6$ lower alcohols such as methanol, ethanol or propanol, tetrahydrofuran, halogenated compounds such as chloroform, methylene chloride, etc. and nitrile compounds such as acetonitrile, etc. The reaction may be conducted in a temperature range from 0° C. to the reflux temperature of the used solvent, specifically from room temperature to 100° C., more specifically from 30 to 60° C.

The azabicyclo[3.1.0]hexanamine compound represented by Formula 6 used as a starting material in Scheme 4 is a novel compound. Accordingly, the azabicyclo[3.1.0]hexanamine compound represented by Formula 6 as a novel intermediate compound and a method for preparing same are included in the scope of the present invention.

The azabicyclo[3.1.0]hexanamine compound represented by Formula 6 may be prepared according to Scheme 7. Specifically, it may be prepared by: 1) converting an azabicyclo[3.1.0]hexanoic acid compound represented by Formula 12 to an azabicyclo[3.1.0]hexanamide compound represented by Formula 14; 2) converting the azabicyclo[3.1.0]hexanamide compound represented by Formula 14 to an azabicyclo[3.1.0]hexanamide salt compound represented by Formula 15; 3) converting the azabicyclo[3.1.0]hexanamide salt compound represented by Formula 15 to a 3-substituted azabicyclo[3.1.0]hexane compound represented by Formula 16; and 4) converting the 3-substituted azabicyclo[3.1.0]hexane compound represented by Formula 16 to the azabicyclo[3.1.0]hexanamine compound represented by Formula 6.

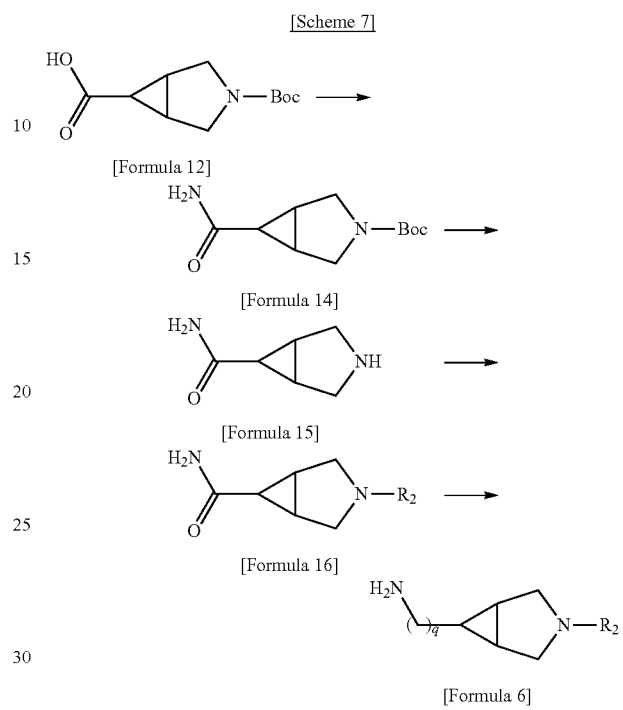

[Scheme 7]

In Scheme 7, $R_2$ and q are the same as described above.

The method for preparing the azabicyclo[3.1.0]hexanamine compound represented by Formula 6 according to Scheme 7 will be described in further detail.

The conversion to the azabicyclo[3.1.0]hexanamide compound represented by Formula 14 is achieved by reacting the azabicyclo[3.1.0]hexanoic acid compound represented by Formula 12, which is obtained from hydrolysis of an ester compound, with ammonia dissolved in methanol by amide coupling.

And, the conversion to the azabicyclo[3.1.0]hexane salt compound represented by Formula 15 is achieved by removing the Boc protecting group from the azabicyclo[3.1.0]hexanamide compound represented by Formula 14.

And, the conversion to the 3-substituted azabicyclo[3.1.0]hexane compound represented by Formula 16 is achieved by introducing various substituents $R_2$ as described in Schemes 1-3. Specifically, the compound is obtained from reaction with the aldehyde compound represented by Formula 3, the acyl halide compound represented by Formula 4 or the sulfonyl halide compound represented by Formula 5.

And, the conversion to the azabicyclo[3.1.0]hexanamine compound represented by Formula 6 is achieved by reducing the 3-substituted azabicyclo[3.1.0]hexane compound represented by Formula 16. A reducing agent used for the reduction may be one used for hydrogenation in the presence of various inorganic catalysts. The reducing agent may be a metal hydride which is commercially available or can be prepared according methods known in the art. Specifically, lithium aluminum hydride (LAH) may be used as the reducing agent.

In the preparation method according to Scheme 7, an inert organic solvent commonly used in the art, which does not affect the reactions, may be used as a reaction solvent. Specific examples of the organic solvent that can be used in the present invention include diethyl ether, $C_1$-$C_6$ lower alcohols such as methanol, ethanol or propanol, tetrahydrofuran, halogenated compounds such as chloroform, methylene chloride, etc. and nitrile compounds such as acetonitrile, etc. The reaction may be conducted in a temperature range from 0° C. to the reflux temperature of the used solvent, specifically from room temperature to 100° C., more specifically from 30 to 60° C.

Since the 6-pyrazolylamido-3-substituted azabicyclo[3.1.0]hexane derivative represented by Formula 1 according to the present invention or a pharmaceutically acceptable salt thereof exhibits activity as a T-type calcium channel antagonist, the present invention provides a pharmaceutical composition containing the novel compound represented by Formula 1 as an active ingredient. The pharmaceutical composition containing the 6-pyrazolylamido-3-substituted azabicyclo[3.1.0]hexane derivative represented by Formula 1 according to the present invention or a pharmaceutically acceptable salt is useful for treating and preventing cerebral diseases, cardiac diseases, cancers or pain-related diseases owing to its antagonistic activity against the T-type calcium channel. Specific examples of the diseases that can be treated or prevented with the pharmaceutical composition according to the present invention include cerebral diseases such as epilepsy, depression, dementia, sleep disorder, diabetes, obesity, etc., cardiac diseases such as hypertension, cardiac dysrhythmia, angina, myocardial infarction, congestive heart failure, etc., cancers such as liver cancer, lung cancer, colon cancer, prostate cancer, breast cancer, uterine cancer, esophageal cancer, brain cancer, etc. and pain-related diseases such as chronic and acute pain, neuropathic pain, etc.

The pharmaceutical composition of the present invention may be prepared into formulations for oral or parenteral administration common in the art, e.g. tablet, capsule, troche, liquid, suspension, etc., by adding commonly used pharmaceutically acceptable, nontoxic carrier, adjuvant, excipient, etc. to the compound represented by Formula 1. The administration dosage of the compound represented by Formula 1 for a human patient may vary depending on the age, body weight and sex of the patient, administration type, physical condition, severity of disease, or the like. A general dosage for an adult patient weighing 70 kg is 0.01-400 mg/day. The administration can be made once or several times a day at the discretion of a physician or a pharmacist.

EXAMPLES

The present invention will be described in more detail through examples. The following examples are for illustrative purposes only and it will be apparent to those skilled in the art not that the scope of this invention is not limited by the examples.

Examples

Example 1 tert-Butyl 2H-pyrrole-1(5H)-carboxylate

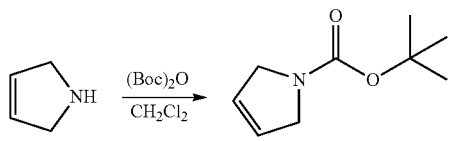

21.1 mL of methylene chloride was added to 3-pyrroline (2.7 mL, 30 mmol) under nitrogen atmosphere and di-tert-butyl dicarbonate (7.8 mL, 36.3 mmol) dissolved in 10.5 mL of methylene chloride was slowly added dropwsie at 0° C. 5 minutes later, the mixture was stirred at room temperature for 18 hours and 30 minutes. The completion of the reaction was confirmed by TLC (hexane:ethyl acetate=10:1). After the reaction was completed, the reaction mixture was concentrated under reduced pressure and separated by column chromatography (hexane:ethyl acetate=10:1) to obtain 5.1 g (100%) of the target compound.

$^1$H NMR (300 MHz, CDCl$_3$) δ 5.84-5.77 (m, 2H), 4.18-4.12 (m, 4H), 1.52 (s, 9H).

Example 2 tert-Butyl 6-ethoxycarbonyl-3-azabicyclo[3.1.0]hexane-3-carboxylate

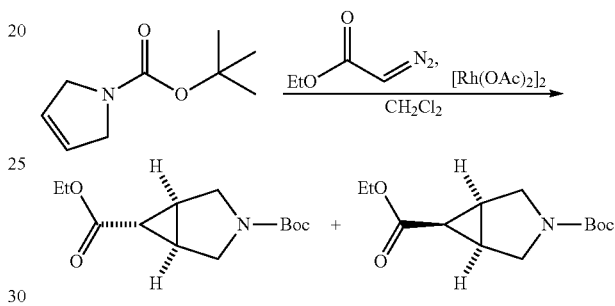

The tert-butyl 2H-pyrrole-1(5H)-carboxylate (1.28 g, 7.59 mmol) prepared in Example 1 and rhodium(II) acetate (168 mg, 0.379 mmol) were added to 25.7 mL of methylene chloride and stirred under nitrogen atmosphere. Then, ethyl diazoate (1.04 mL, 9.86 mmol) dissolved in 11 mL of methylene chloride was slowly added dropwsie for 2 hours and 10 minutes. After stirring for 21 hours, the mixture was filtered through Celite and concentrated under reduced pressure. The reaction mixture was separated by column chromatography (hexane:ethyl acetate=6:1→3:1) to obtain 837.6 mg (43.3%) of an exo-isomer and 436.1 mg (22.5%) of an endo-isomer as the target compound.

$^1$H NMR exo-isomer (300 MHz, CDCl$_3$) δ 4.17 (q, J=7.14 Hz, 2H), 3.72 (d, J=11.2 Hz, 1H), 3.64 (d, J=11.2 Hz, 1H), 3.46-3.43 (m, 2H), 2.10 (br, 2H), 1.52-1.50 (m, 1H), 1.47 (s, 9H), 1.30 (t, J=7.14 Hz, 3H).

$^1$H NMR endo-isomer (300 MHz, CDCl$_3$) δ 4.14 (q, J=7.11 Hz, 2H), 3.80 (dd, J=11.2, 16.1 Hz, 2H), 3.46 (brt, J=9.81 Hz, 2H), 1.92-1.88 (m, 2H), 1.80 (dd, J=7.02, 8.99 Hz, 1H), 1.47 (s, 9H), 1.29 (t, J=7.14 Hz, 3H).

Example 3

3-(tert-Butoxycarbonyl)-3-azabicyclo[3.1.0]hexane-6-carboxylic acid

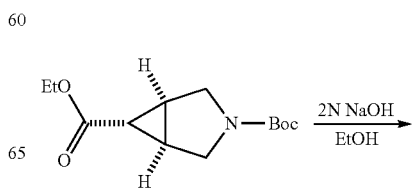

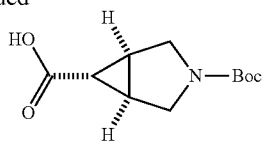

The tert-butyl 6-ethoxycarbonyl-3-azabicyclo[3.1.0]hexane-3-carboxylate exo-isomer (613 mg, 2.40 mmol) prepared in Example 2 was dissolved in 6 mL of ethanol and 2N NaOH (2.40 mL, 4.80 mmol) was added dropwsie at 0° C. After stirring at room temperature for 3 hours, the completion of the reaction was confirmed by TLC (hexane:ethyl acetate=6:1). After the reaction was completed, the reaction mixture was concentrated under reduced pressure and then extracted by adding methylene chloride and water. After removing the organic layer containing byproducts, the aqueous layer was acidified with 1N HCl and extracted with methylene chloride. The organic layer was dried with anhydrous magnesium sulfate, filtered and concentrated under reduced pressure to obtain 527 mg (96.5%) of the target compound.

$^1$H NMR (300 MHz, CDCl$_3$) δ 3.74 (d, J=11.1 Hz, 1H), 3.66 (d, J=11.3 Hz, 1H), 3.53-3.45 (m, 2H), 2.17 (br, 2H), 1.55-1.53 (m, 1H), 1.48 (s, 9H).

Example 4 tert-Butyl 6-carbamoyl-3-azabicyclo[3.1.0]hexane-3-carboxylate

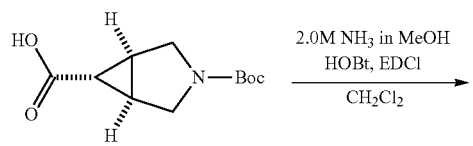

The 3-(tert-butoxycarbonyl)-3-azabicyclo[3.1.0]hexane-6-carboxylic acid (252 mg, 1.11 mmol) prepared in Example 3, benzotriazole (180 mg, 1.33 mmol) and 1-ethyl-3-(3-dimethylaminopropyl)carbodiimide (255 mg, 1.33 mmol) were dissolved in 3.0 mL of methylene chloride and diisopropylethylamine (232 μL, 1.33 mmol) was added dropwise. After adding 2 M ammonia solution (2.49 mL, 4.98 mmol) dissolved in methanol dropwise at 0° C., the mixture was stirred at room temperature for 4 hours. The completion of the reaction was confirmed by TLC (CH$_2$Cl$_2$:MeOH=15:1). After the reaction was completed, the reaction mixture was diluted with methylene chloride and washed with saturated sodium chloride. The organic layer was dried with anhydrous magnesium sulfate, filtered, concentrated under reduced pressure and separated by column chromatography (CH$_2$Cl$_2$:MeOH=15:1) to obtain 177 mg (70.6%) of the target compound.

$^1$H NMR (300 MHz, CDCl$_3$) δ 5.59 (br, 1H), 5.30 (br, 1H), 3.72 (d, J=10.3 Hz, 1H), 3.63 (d, J=11.2 Hz, 1H), 3.49-3.45 (m, 2H), 2.12 (br, 2H), 1.48 (s, 9H), 1.32 (t, J=2.88 Hz, 1H).

Example 5

3-Azabicyclo[3.1.0]hexane-6-carboxamide hydrochloride

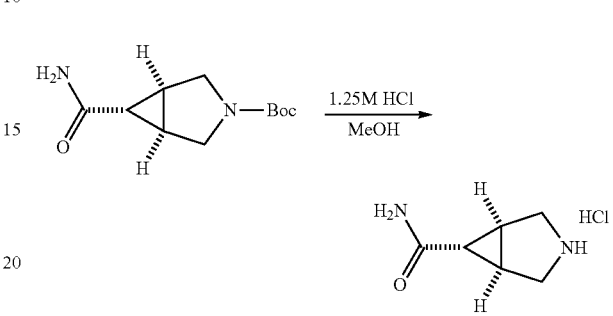

1.25 M hydrochloric acid solution (9.76 mL, 12.2 mmol) dissolved in methanol was added dropwise to the tert-butyl 6-carbamoyl-3-azabicyclo[3.1.0]hexane-3-carboxylate (177 mg, 0.784 mmol) prepared in Example 4 and stirred for 3 hours. The completion of the reaction was confirmed by TLC (CH$_2$Cl$_2$:MeOH=15:1). After the reaction was completed, the reaction mixture was concentrated under reduced pressure to obtain 127 mg (100%) of the target compound.

$^1$H NMR (300 MHz, DMSO) δ 8.90 (br, 1H), 7.58 (br, 1H), 6.96 (br, 1H), 3.30-3.28 (m, 4H), 1.98 (br, 2H), 1.63-1.59 (m, 1H).

Example 6

3-(3,3-Dimethylbutyl)-3-azabicyclo[3.1.0]hexane-6-carboxamide

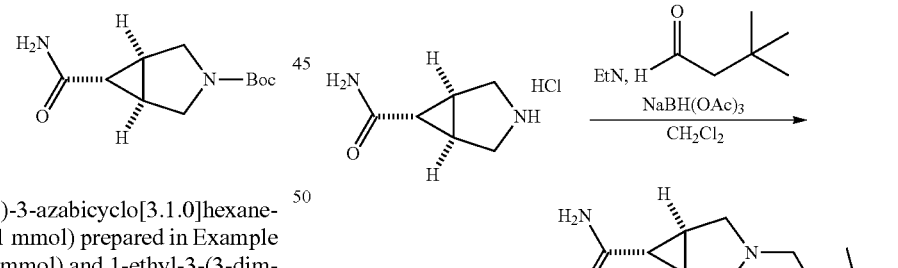

The 3-azabicyclo[3.1.0]hexane-6-carboxamide hydrochloride (169 mg, 1.04 mmol) prepared in Example 5 and a molecular sieve were dried in vacuum and dissolved in 5 mL of methylene chloride. Then, triethylamine (151 μL, 1.08 mmol) was added dropwise at 0° C. After adding 3,3-dimethylbutyraldehyde (135 μL, 1.08 mmol), the mixture was stirred at room temperature for 1 hour. After adding sodium triacetoxyborohydride (687 mg, 3.24 mmol) and then adding 10 mL of methylene chloride, the mixture was stirred for 2 hours and 30 minutes. The completion of the reaction was confirmed by TLC (CH$_2$Cl$_2$:MeOH=10:1). After the reaction was completed, the reaction mixture was diluted with methylene chloride and extracted several times with saturated sodium bicarbonate. The organic layer was dried with anhydrous magnesium sulfate, filtered, concentrated under reduced pressure and separated by column chromatography (CH$_2$Cl$_2$: MeOH=10:1) to obtain 173 mg (79.2%) of the target compound.

$^1$H NMR (300 MHz, CDCl$_3$) δ 5.83 (br, 2H), 3.15 (d, J=9.24 Hz, 2H), 2.45 (t, J=8.34 Hz, 2H), 2.40 (d, J=9.18 Hz, 2H), 1.96 (br, 2H), 1.91-1.90 (m, 1H), 1.36 (t, J=8.07 Hz, 2H), 0.91 (s, 9H).

Example 7

(3-(3,3-Dimethylbutyl)-3-azabicyclo[3.1.0]hexane-6-yl)methanamine

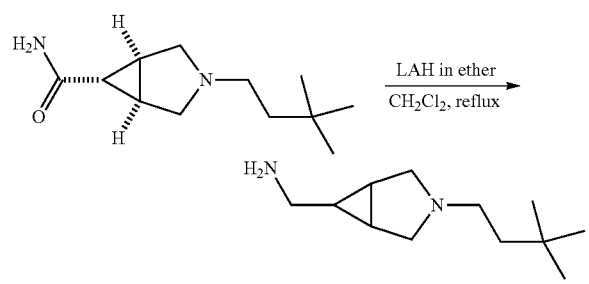

The 3-(3,3-dimethylbutyl)-3-azabicyclo[3.1.0]hexane-6-carboxamide (170 mg, 0.808 mmol) prepared in Example 6 was dissolved in 7.42 mL of methylene chloride and 1 M lithium aluminum hydride (LAH; 3.23 mL, 3.23 mmol) dissolved in diethyl ether was added dropwise at 0° C. After stirring for 5 minutes, the mixture was heated to room temperature. 15 minutes later, the mixture was stirred for 23 hours at 55° C. under reflux. The completion of the reaction was confirmed by TLC (CH$_2$Cl$_2$:MeOH=10:1). After the reaction was completed, sodium sulfate hydrate was cautiously added at 0° C. The reaction mixture was filtered sequentially through Celite and anhydrous sodium sulfate, concentrated under reduced pressure and dried to obtain 130 mg (82.0%) of the target compound.

$^1$H NMR (300 MHz, CDCl$_3$) δ 3.09 (d, J=8.79 Hz, 2H), 2.53 (d, J=6.96 Hz, 2H), 2.44 (t, J=8.04 Hz, 2H), 2.32 (d, J=8.16 Hz, 2H), 1.50 (br, 2H), 1.39 (t, J=8.31 Hz, 2H), 1.34-1.29 (m, 1H), 1.24 (br, 2H), (s, 9H).

Example 8

5-Isobutyl-1-phenyl-pyrazole-3-oxime

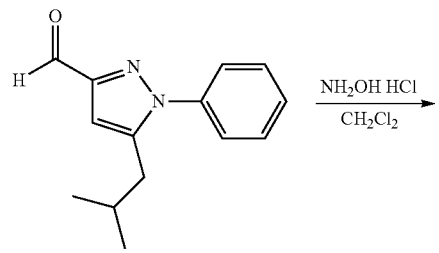

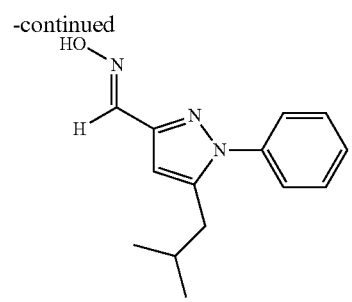

NH$_2$OH.HCl (135.8 mg, 1.95 mmol) was dissolved in 1.7 mL of methylene chloride and triethylamine (272 µL, 1.95 mmol) was added dropwise while stirring. When the pH reached 7,3-formyl-5-isobutyl-1-phenylpyrazole (405 mg, 1.77 mmol) dissolved in methylene chloride was added dropwise. After stirring for 1 hour, the completion of the reaction was confirmed by TLC (hexane:ethyl acetate=1:1). After the reaction was completed, the reaction mixture was extracted with methylene chloride after adding water. The organic layer was dried with anhydrous magnesium sulfate, filtered, concentrated under reduced pressure and dried to obtain 427 mg (98.9%) of the target compound.

$^1$H NMR (400 MHz, CDCl$_3$) δ 8.22 (s, 1H), 7.51-7.40 (m, 5H), 7.21 (br, 1H), 6.53 (s, 1H), 2.52 (d, J=7.16 Hz, 2H), 1.88-1.80 (m, 1H), 0.88 (d, J=6.60 Hz, 6H).

Example 9

(5-Isobutyl-3-aminomethyl-1-phenyl)pyrazole

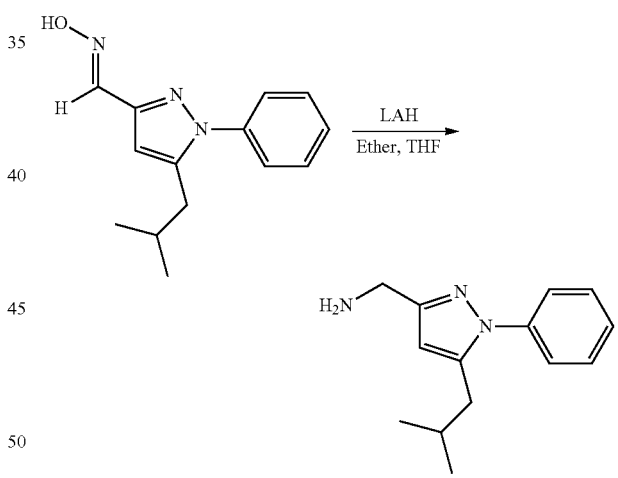

The 5-isobutyl-1-phenyl-pyrazole-3-oxime (1.22 g, 5.02 mmol) prepared in Example 8 was dried in vacuum and dissolved in 6 mL of diethyl ether and 1.5 mL of THF under nitrogen atmosphere. Then, 1 M LAH (11.0 mL, 11.0 mmol) dissolved in diethyl ether was added dropwise at 0° C. After stirring for 30 minutes, the mixture was stirred at room temperature for 3 hours. The completion of the reaction was confirmed by TLC (hexane:ethyl acetate=1:1). After the reaction was completed, sodium sulfate hydrate was cautiously added at 0° C. The reaction mixture was filtered sequentially through Celite and anhydrous sodium sulfate, concentrated under reduced pressure and dried to obtain 1.06 g (92.1%) of the target compound.

$^1$H NMR (400 MHz, CDCl$_3$) δ 7.48-7.36 (m, 5H), 6.14 (s, 1H), 3.91 (s, 2H), 2.50 (d, J=7.12 Hz, 2H), 1.88-1.80 (m, 1H), 0.87 (d, J=6.64 Hz, 6H).

Example 10 tert-Butyl 6((5-isobutyl-1-phenyl-1H-pyrazole-3-yl)methylcarbamoyl)-3-azabicyclo[3.1.0]hexane-3-carboxylate

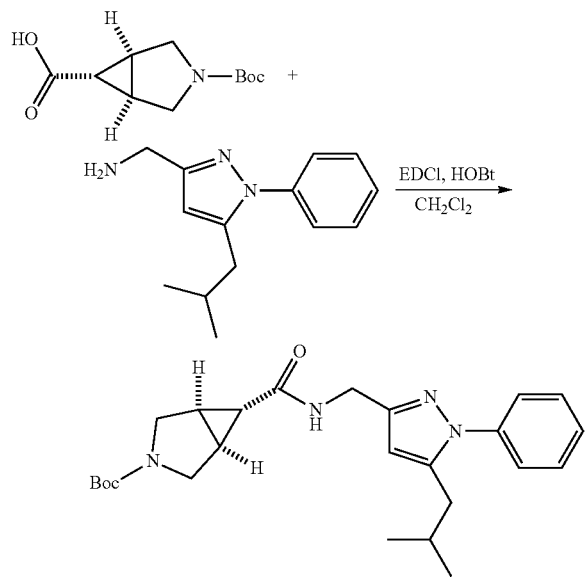

The 3-(tert-butoxycarbonyl)-3-azabicyclo[3.1.0]hexane-6-carboxylic acid (185 mg, 0.812 mmol) prepared in Example 3, hydroxybenzotriazole (132 mg, 0.975 mmol) and 1-ethyl-3-(3-dimethylaminopropyl)carbodiimide (187 mg, 0.975 mmol) were dissolved in 3.0 mL of methylene chloride and the (5-isobutyl-3-aminomethyl-1-phenyl)pyrazole (205 mg, 0.894 mmol) prepared in Example 9 was added dropwise. After stirring for 3 hours, the completion of the reaction was confirmed by TLC (hexane:ethyl acetate=1:2). After the reaction was completed, the mixture was extracted with methylene chloride after adding water and saturated sodium bicarbonate. The organic layer was dried with anhydrous sodium sulfate, filtered, concentrated under reduced pressure and separated by column chromatography (hexane:ethyl acetate=1:2) to obtain 328 mg (92.1%) of the target compound.

$^1$H NMR (300 MHz, CDCl$_3$) δ 7.54-7.40 (m, 5H), 6.26 (br, 1H), 6.17 (s, 1H), 4.53 (d, J=5.01 Hz, 2H), 3.69 (d, J=11.9 Hz, 1H), 3.60 (d, J=11.1 Hz, 1H), 3.47-3.43 (m, 2H), 2.53 (d, J=7.14 Hz, 2H), 2.12 (br, 2H), 1.90-1.81 (m, 1H), 1.47 (s, 9H), 1.29 (t, J=3.27 Hz, 1H), 0.90 (d, J=6.60 Hz, 6H).

Example 11

6-((5-Isobutyl-1-phenyl-1H-pyrazole-3-yl)methylcarbamoyl)-3-azabicyclo[3.1.0]hexane hydrochloride

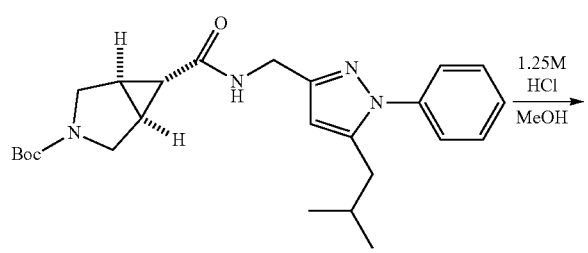

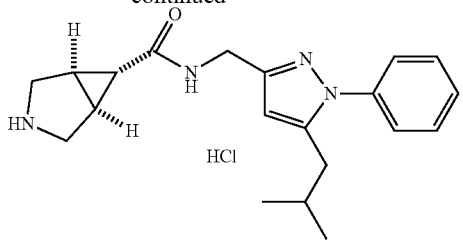

1.25 M hydrochloric acid solution (9.76 mL, 12.2 mmol) dissolved in methanol was added dropwise to the tert-butyl 6-((5-isobutyl-1-phenyl-1H-pyrazole-3-yl)methylcarbamoyl)-3-azabicyclo[3.1.0]hexane-3-carboxylate (268 mg, 0.610 mmol) prepared in Example 10 and stirred for 3 hours. The completion of the reaction was confirmed by TLC (hexane:ethyl acetate=1:2). After the reaction was completed, the reaction mixture was concentrated under reduced pressure to obtain 229 mg (100%) of the target compound.

$^1$H NMR (300 MHz, CDCl$_3$) δ 10.6 (br, 1H), 9.38 (br, 1H), 8.02 (br, 1H), 7.69-7.63 (m, 3H), 7.54-7.52 (m, 2H), 6.45 (s, 1H), 4.66 (d, J=4.56 Hz, 2H), 3.50 (br, 4H), 2.52 (d, J=7.02 Hz, 2H), 2.21 (br, 3H), 1.95-1.86 (m, 1H), 0.92 (d, J=6.54 Hz, 6H).

Example 12

3-[3-(3,3-Dimethylbutyl)-3-azabicyclo[3.1.0]hexane-6-carboxamido]methyl-5-isobutyl-1-phenyl-1H-pyrazole (Compound 1)

The 6-((5-isobutyl-1-phenyl-1H-pyrazole-3-yl)methylcarbamoyl)-3-azabicyclo[3.1.0]hexane hydrochloride (93.5 mg, 0.249 mmol) prepared in Example 11 and a molecular sieve were dried in vacuum and dissolved in 2 mL of methylene chloride. Then, triethylamine (35 μL, 0.249 mmol) was added dropwise at 0° C. After adding 3,3-dimethylbutyraldehyde (31 μL, 0.249 mmol) dropwise, the mixture was stirred at room temperature for 1 hour. After adding sodium triacetoxyborohydride (159 mg, 0.748 mmol), the mixture was stirred for 2 hours and 30 minutes. The completion of the reaction was confirmed by TLC (hexane:ethyl acetate=1:2). After the reaction was completed, the reaction mixture was diluted with methylene chloride and extracted several times with saturated sodium bicarbonate. The organic layer was dried with anhydrous magnesium sulfate, filtered, concentrated under reduced pressure and separated by column chromatography (CH$_2$Cl$_2$:MeOH=15:1) to obtain 67.3 mg (63.9%) of the target compound.

$^1$H NMR (300 MHz, CDCl$_3$) δ 7.53-7.40 (m, 5H), 6.24 (br, 1H), 6.16 (s, 1H), 4.50 (d, J=5.07 Hz, 2H), 3.11 (d, J=9.03 Hz, 2H), 2.53 (d, J=7.14 Hz, 2H), 2.42 (t, J=8.40 Hz, 2H), 2.36 (d, J=8.79 Hz, 2H), 1.99 (s, 2H), 1.89-1.80 (m, 2H), 1.35 (t, J=8.40 Hz, 2H), 0.90 (s, 9H), 0.89 (d, J=7.32 Hz, 6H).

$^{13}$C NMR (75 MHz, CDCl$_3$) δ 172.5, 162.3, 149.4, 144.3, 139.8, 129.1, 128.0, 125.7, 104.8, 54.9, 51.5, 42.4, 37.8, 35.2, 29.8, 29.6, 28.4, 25.1, 23.8, 22.4.

Example 13

3-(3-Benzyl-3-azabicyclo[3.1.0]hexane-6-carboxamido)methyl-5-isobutyl-1-phenyl-1H-pyrazole (Compound 2)

The target compound was prepared in the same manner as in Example 12.

Yield: 75.7%.

$^1$H NMR (300 MHz, CDCl$_3$) δ 7.53-7.40 (m, 5H), 7.34-7.22 (m, 5H), 6.43 (br, 1H), 6.17 (s, 1H), 4.51 (d, J=5.07 Hz,

2H), 3.61 (s, 2H), 3.02 (d, J=8.97 Hz, 2H), 2.52 (d, J=7.14 Hz, 2H), 2.45 (d, J=8.49 Hz, 2H), 1.99 (s, 2H), 1.95 (s, 1H), 1.91-1.78 (m, 1H), 0.89 (d, J=6.6 Hz, 6H).

$^{13}$C NMR (75 MHz, CDCl$_3$) δ 172.6, 149.5, 144.3, 139.9, 139.4, 129.1, 128.5, 128.2, 128.0, 126.9, 125.8, 104.8, 58.8, 54.3, 37.8, 35.2, 28.4, 25.2, 23.6, 22.4.

Example 14

5-Isobutyl-1-phenyl-3-{3-[4-(trifluoromethyl)phenylethyl]-3-azabicyclo[3.1.0]hexane-6-carboxamido}methyl-1H-pyrazole (Compound 3)

The target compound was prepared in the same manner as in Example 12.
Yield: 35.2%.
$^1$H NMR (300 MHz, CDCl$_3$) δ 7.57-7.40 (m, 7H), 7.32-7.30 (m, 2H), 6.26 (t, J=4.68 Hz, 1H), 6.17 (s, 1H), 4.51 (d, J=5.10 Hz, 2H), 3.13 (d, J=8.88 Hz, 2H), 2.80 (t, J=6.84 Hz, 2H), 2.71 (t, J=7.13 Hz, 2H), 2.53 (d, J=7.17 Hz, 2H), 2.46 (d, J=8.60 Hz, 2H), 2.01 (s, 2H), 1.90-1.82 (m, 1H), 1.80 (s, 1H), 0.90 (d, J=6.60 Hz, 6H).
$^{13}$C NMR (75 MHz, CDCl$_3$) δ 172.4, 149.4, 144.6, 144.3, 139.8, 129.1, 128.9, 128.5, 128.0, 126.2, 125.7, 125.2, 125.1, 125.1, 122.6, 104.8, 56.1, 54.6, 37.7, 35.2, 28.4, 25.1, 23.7, 22.4.

Example 15

3-(3-Benzoyl-3-azabicyclo[3.1.0]hexane-6-carboxamido)methyl-5-isobutyl-1-phenyl-1H-pyrazole (Compound 4)

The 6-((5-isobutyl-1-phenyl-1H-pyrazole-3-yl)methylcarbamoyl)-3-azabicyclo[3.1.0]hexane hydrochloride (367 mg, 0.979 mmol) prepared in Example 11 was dissolved in 4.9 mL of methylene chloride and triethylamine (273 μL, 1.96 mmol) was added dropwise at 0° C. After stirring for 5 minutes, benzoyl chloride (125 μL, 1.08 mmol) was added dropwise. 10 minutes later, after stirring at room temperature for 3 hours, the completion of the reaction was confirmed by TLC (CH$_2$Cl$_2$:MeOH=20:1). After the reaction was completed, the reaction mixture was extracted with methylene chloride after adding water, 1 N HCl and saturated sodium bicarbonate. The organic layer was dried with anhydrous magnesium sulfate, filtered, concentrated under reduced pressure and separated by column chromatography (CH$_2$Cl$_2$:MeOH=20:1) to obtain 360 mg (83.2%) of the target compound.
$^1$H NMR (300 MHz, CDCl$_3$) δ 7.48-7.30 (m, 10H), 6.94 (t, J=4.98 Hz, 1H), 6.13 (s, 1H), 4.45 (d, J=5.1 Hz, 2H), 4.19 (d, J=12.4 Hz, 1H), 3.66 (dd, J=3.06, 10.9 Hz, 1H), 3.55-3.47 (m, 2H), 2.48 (d, J=7.14 Hz, 2H), 2.10 (d, J=10.2 Hz, 2H), 1.85-1.76 (m, 1H), 1.31 (t, J=3.0 Hz, 1H), 0.85 (d, J=6.6 Hz, 6H).
$^{13}$C NMR (75 MHz, CDCl$_3$) δ 170.6, 170.3, 149.2, 144.3, 139.7, 136.6, 130.0, 129.1, 128.3, 128.1, 127.0, 125.8, 104.8, 51.1, 47.6, 37.7, 35.1, 28.4, 25.4, 25.1, 23.7, 22.4.

Example 16

5-Isobutyl-1-phenyl-3-[3-(2-phenylacetyl)-3-azabicyclo[3.1.0]hexane-6-carboxamido]methyl-1H-pyrazole (Compound 5)

The target compound was prepared in the same manner as in Example 15.
Yield: 82.1%.
$^1$H NMR (300 MHz, CDCl$_3$) δ 7.51-7.22 (m, 10H), 6.67 (t, J=4.98 Hz, 1H), 6.15 (s, 1H), 4.47 (d, J=5.16 Hz, 2H), 3.85 (d, J=12.3 Hz, 1H), 3.65-3.56 (m, 4H), 3.49 (td, J=3.9, 12.3 Hz, 1H), 2.50 (d, J=7.17 Hz, 2H), 2.16-2.07 (m, 2H), 1.87-1.78 (m, 1H), 1.17 (t, J=3.06 Hz, 1H), 0.88 (d, J=6.6 Hz, 6H).
$^{13}$C NMR (75 MHz, CDCl$_3$) δ 170.6, 170.2, 149.1, 144.4, 139.7, 134.4, 129.2, 128.9, 128.7, 128.2, 126.9, 125.8, 104.9, 49.0, 48.1, 42.3, 37.7, 35.1, 28.4, 26.5, 25.3, 24.1, 22.4.

Example 17

5-Isobutyl-1-phenyl-3-(3-benzenesulfonyl-3-azabicyclo[3.1.0]hexane-6-carboxamido)methyl-1H-pyrazole (Compound 6)

The 6-((5-isobutyl-1-phenyl-1H-pyrazole-3-yl)methylcarbamoyl)-3-azabicyclo[3.1.0]hexane hydrochloride (69.5 mg, 0.185 mmol) prepared in Example 11 was dissolved in 2.0 mL of methylene chloride and triethylamine (54.3 μL, 0.389 mmol) was added dropwise at 0° C. After stirring for 5 minutes, benzenesulfonyl chloride (24.9 μL, 0.195 mmol) was added dropwise. 10 minutes later, after stirring at room temperature for 1 hour, the completion of the reaction was confirmed by TLC (hexane:ethyl acetate=1:2). After the reaction was completed, the reaction mixture was extracted with methylene chloride after adding water and saturated sodium bicarbonate. The organic layer was dried with anhydrous magnesium sulfate, filtered, concentrated under reduced pressure and separated by column chromatography (hexane:ethyl acetate=1:1→1:2) to obtain 70.4 mg (79.4%) of the target compound.
$^1$H NMR (300 MHz, CDCl$_3$) δ 7.79 (d, J=8.01 Hz, 2H), 7.62-7.37 (m, 8H), 6.73 (br, 1H), 6.15 (s, 1H), 4.46 (d, J=5.07 Hz, 2H), 3.59 (d, J=9.51 Hz, 2H), 3.09 (d, J=9.3 Hz, 2H), 2.51 (d, J=7.17 Hz, 2H), 2.01 (s, 2H), 1.89-1.75 (m, 1H), 1.52 (t, J=2.88 Hz, 1H), 0.87 (d, J=6.6 Hz, 6H).
$^{13}$C NMR (75 MHz, CDCl$_3$) δ 170.5, 149.0, 144.4, 139.8, 136.1, 132.9, 129.2, 129.1, 128.1, 127.5, 125.8, 104.8, 49.6, 37.8, 35.1, 28.4, 24.5, 24.3, 22.4.

Example 18

3-{2-[3-(3,3-Dimethylbutyl)-3-azabicyclo[3.1.0]hexane-6-yl]methyl}carbamoyl-5-isobutyl-1-phenyl-1H-pyrazole (Compound 7)

5-Isobutyl-1-phenylpyrazole-3-carboxylic acid (75.3 mg, 0.307 mmol), hydroxybenzotriazole (50.0 mg, 0.369 mmol) and 1-ethyl-3-(3-dimethylaminopropyl)carbodiimide (71.0 mg, 0.369 mmol) were dissolved in 3.0 mL of methylene chloride and the (3-(3,3-dimethylbutyl)-3-azabicyclo[3.1.0]hexane-6-yl)methanamine (60.3 mg, 0.307 mmol) prepared in Example 7 was added dropwise. After stirring for 3 hours and 30 minutes, the completion of the reaction was confirmed by TLC (CH$_2$Cl$_2$:MeOH=13:1). After the reaction was completed, the reaction mixture was extracted with methylene chloride after adding water and saturated sodium bicarbonate. The organic layer was dried with anhydrous sodium sulfate, filtered, concentrated under reduced pressure and separated by column chromatography (CH$_2$Cl$_2$:MeOH=13:1) to obtain 109 mg (84.2%) of the target compound.
$^1$H NMR (300 MHz, CDCl$_3$) δ 7.48-7.34 (m, 5H), 7.01 (br, 1H), 6.71 (s, 1H), 3.23 (t, J=6.09 Hz, 2H), 3.00 (d, J=8.73 Hz, 2H), 2.47 (d, J=7.02 Hz, 2H), 2.34 (t, J=8.13 Hz, 2H), 2.22 (d, J=8.49 Hz, 2H), 1.84-1.75 (m, 1H), 1.37 (br, 1H), 1.30 (br, 4H), 0.83 (br, 15H).
$^{13}$C NMR (75 MHz, CDCl$_3$) δ 162.0, 146.8, 144.9, 139.4, 129.2, 128.6, 125.9, 106.5, 55.1, 51.6, 42.3, 41.4, 35.1, 29.7, 29.6, 28.2, 22.3, 21.6, 19.7.

Formulation Examples

The novel compound represented by Formula 1 according to the present invention can be prepared into various formulations depending on purposes. The followings are some exemplary formulation examples containing the compound represented by Formula 1 as an active ingredient. It will be apparent to those skilled in the art not that the scope of this invention is not limited by the examples.

Formulation 1: Tablet (Direct Compression)

5.0 mg of the active ingredient was sieved, mixed with 14.1 mg of lactose, 0.8 mg of crospovidone USNF and 0.1 mg of magnesium stearate and prepared into a tablet by compression.

Formulation 2: Tablet (Wet Granulation)

5.0 mg of the active ingredient was sieved and mixed with 16.0 mg of lactose and 4.0 mg of starch. After adding an adequate amount of a solution of 0.3 mg of polysorbate 80 dissolved in pure water, the mixture was granulated. After drying, the as-obtained granule was sieved and mixed with 2.7 mg of colloidal silicon dioxide and 2.0 mg of magnesium stearate. The granule was prepared into a tablet by compression.

Formulation 3: Powder and Capsule 5.0 mg of the active ingredient was sieved and mixed with 14.8 mg of lactose, 10.0 mg of polyvinylpyrrolidone and 0.2 mg of magnesium stearate. The mixture was filled in a hard No. 5 gelatin capsule using an adequate apparatus.

Formulation 4: Injection

An injection was prepared using 100 mg of the active ingredient, 180 mg of mannitol, 26 mg of $Na_2HPO_4 \cdot 12H_2O$ and 2974 mg of distilled water.

Test Examples

Test Example 1. Test of Antagonistic Activity Against T-Type Calcium Channel

The novel compounds represented by Formula 1 according to the present invention were tested for the antagonistic activity against the T-type calcium channel as follows.

First, through primary screening, compounds exhibiting 40% or higher antagonistic activity against the T-type calcium channel were selected from the synthesized compounds using the high-throughput screening (HTS) device FDSS6000. Then, as secondary screening, the effective inhibitory concentration $IC_{50}$ for human HEK293 cells was obtained by measuring the potential of $Ca^{2+}$.

1) Measurement of T-Type Calcium Channel Activity Using FDSS6000

12-24 hours prior to the activity assay, HEK293 cells ($\alpha_{1G}$ cell line: KCTC 10519BP, Gene Bank, Korea Research Institute of Bioscience and Biotechnology) in which both α1G T-type calcium channels and $K_{ir}2.1$ channels are stably expressed were seeded onto a 96-well plate coated with poly-L-lysine (0.05 mg/mL) at a density of $4 \times 10^4$ cells/well using a cell distributor (Titertek). On the following day, the cells attached onto the 96-well plate well washed three times with HEPES buffer (150 mM NaCl, 5 mM KCl, 1 mM $MgCl_2$, 2 mM $CaCl_2$, 10 mM HEPES, 10 mM glucose, pH 7.4) using an automatic 96-well plate washer (BioTek), labeled with a fluorescent dye by incubating in HEPES buffer containing 5 µM fluo-3/AM and 0.001% Pluronic F-127 at room temperature for 1 hour and then washed again with HEPES buffer twice. Subsequently, 10 minutes prior to the FDSS6000 measurement, the cells were washed with HEPES buffer containing 10 mM $CaCl_2$ once and the final volume was adjusted to 81 µL. Separately from the 96-well plate with the cells, two 96-well drug plates were prepared, one containing KCl (final concentration 75 mM) for activating the T-type calcium channel and the other containing the blocking agent (test compound). Since most cell-based HTS devices are provided with a fluid application system for drug injection but not with a liquid absorption system, the KCl solution and the blocking agent to be screened were prepared at high concentrations 5 times the final concentrations in 10 mM $CaCl_2$ HEPES buffer with a volume of 27 µL and then diluted to ⅕ for measurement of activity to a final volume of 135 µL. For the FDSS6000 measurement, after baseline recording for 20 seconds, the cells were pretreated with the test compound for 75 seconds and the change in intracellular calcium concentration induced by KCl was measured. The % inhibition by the test compound was calculated as integrated values of the 340/380 ratio relative to the untreated control group. 10 µM mibefradil was used as the control drug.

For calcium imaging, the cells were selectively exposed to light of excitation wavelengths (340 nm and 380 nm) with four xenon lamps installed in the FDSS6000 device using a computer-controlled filter wheel. The emitted fluorescence light that passed through a 515 nm long-pass filter was passed through a freezing CCD camera mounted in the device. Data were recorded every 1.23 seconds and an average value of the 340/380 ratio for each well of the 96-well plate was obtained using a digital fluorescence analyzer. All the data were analyzed using a FDSS6000-dedicated program provided by Hamamatsu Photonics.

2) Measurement of T-Type Calcium Channel Activity in HEK293 Cells by Whole-Cell Patch Clamp Electrophysiology HEK293 cells were cultured in Dulbecco's modified Eagle's medium (DMEM) containing 10% fetal bovine serum (FBS), 1% penicillin/streptomycin (v/v) in an incubator at 36.5° C. under a humidified condition of 95% air/5% $CO_2$. The culture medium was replaced with a fresh one every 3-4 days and the cells were subcultured every week. Only the cells that express the $\alpha_{1G}$ T-type calcium channel were allowed to grow selected using G-418 (0.5 mg/mL). The cells were incubated on a cover slip coated with poly-L-lysine (0.5 mg/mL) for 2-7 days prior to recording of the T-type calcium channel activity. The T-type calcium channel current at single cell level was measured by whole-cell patch clamp electrophysiology using an EPC-9 amplifier (HEKA, Germany). For the T-type calcium channel activity measurement, an extracellular solution (140 mM NaCl, 2 mM $CaCl_2$, 10 mM HEPES, pH 7.4) and an intracellular solution (130 mM KCl, 10 mM HEPES, 11 mM EGTA, 5 mM MgATP, pH 7.4) were used. To measure the activity of the T-type calcium channel which is activated at low voltage, a single cell was pricked with a glass microelectrode with a resistance of 3-4 MΩ wherein the intracellular solution was filled to make a whole-cell recording mode. Thereafter, the cell membrane potential was fixed to −100 mV and the inward current evoked by the T-type calcium channel activity was measured every 10 seconds at hypopolarization with −30 mV (50 ms duration). Each compound was dissolved in 100% dimethyl sulfoxide (DMSO) to make a 10 mM stock solution. The effect of the compound on the T-type calcium channel current was examined initially at a thousandfold diluted concentration of 10 µM and the $IC_{50}$ value was obtained at other concentrations (0.1-100 µM). More specifically, the cells were treated with each compound together with the extracellular solution for 30-60 seconds and the % inhibition was determined by calculating the inhibition of peak current induced by the compound. The result is shown in Table 1.

TABLE 1

| Test compounds | % inhibition ($\alpha_{1G}$, 10 μM) | % inhibition ($\alpha_{1H}$, 10 μM) |
|---|---|---|
| Compound 1 | 56.89 | 47.99 |
| Compound 2 | 76.43 | 58.67 |
| Compound 3 | 60.50 | 64.58 |
| Compound 4 | 80.40 | 90.27 |
| Compound 5 | 81.01 | 89.88 |
| Compound 6 | 38.24 | 23.70 |
| Compound 7 | 64.29 | 61.87 |

Test Example 2. Test of Neuropathic Pain Inhibition Activity in In-Vivo Animal Model Neuropathic pain was induced in 19 rats, which were selected from 30 rats by performing a behavioral test, by surgical operation. After performing a behavioral test 2 weeks later, 13 rats in which neuropathic pain was successfully induced and the other rats in which neuropathic pain was not successfully induced were grouped randomly. After orally administering 100 mg/kg gabapentin to four rats and 100 mg/kg Compound 1 to six rats, a behavioral test was performed. The result is shown in FIG. 1.

Test Example 3. Anticancer Effect Screening Test

1) Cancer Cell Culture

Human fibroblastoma (HT-1080), human glioma (U87-MG), human prostate carcinoma (LNCaP), human esophageal carcinoma (KYSE410), human lung carcinoma (A-549), human breast cancer (MCF-7) and human liver carcinoma (HepG2) cells were used to test the anticancer activity of the test compounds. All the cancer cells are human-derived tumor cells and were acquired from the Korean Cell Line Bank. The cells were cultured in RPMI 1640 medium containing 10% FBS in an incubator maintained at constant temperature and humidity (37° C., 5% $CO_2$). The cells were subcultured every three days using 0.25% trypsin-1 mM EDTA.

2) Measurement of Anticancer Activity

The sulforhodamine B (SRB) assay technique, which was developed in 1989 by the US National Cancer Institute for measurement of in-vitro anticancer activity of drugs, was used.

The subcultured cells were separated using trypsin-CDTA solution and seeded onto a 96-well microplate at a concentration of 5×10³ cells/well. After incubation in a $CO_2$ incubator for 24 hours, the culture medium was removed and 100 μL of the test compound which was diluted 4-fold was added. After incubation for 48 hours, the cells were fixed by adding 100 μL of formalin solution. Then, the cells were washed 5 times with distilled water and dried at room temperature. After adding 100 μL of 0.4% SRB solution and keeping at room temperature for 30 minutes, the cells were washed 5 times with 1% acetic acid and dried at room temperature. After completely lysing the cells by adding 200 μL of 10 mM Trisma base (pH 10.3) per well, absorbance was measured at 520 nm.

To evaluate the anticancer activity of the test compound against the cancer cells, the $GI_{50}$ value was calculated according to Equation 1 or 2.

$$\text{Anticancer activity (\%)} = (T_2-T_0)/T_0 \times 100 \text{ (if } T_2>T_0) \quad \text{Equation 1}$$

In Equation 1, $T_0$ represents the number of cells before adding the test compound and $T_2$ represents the number of cells after adding the test compound and incubating for 48 hours.

$$\text{Anticancer activity (\%)} = (T_2-T_0)/(C-T_0) \times 100 \text{ (if } T_2=T_0 \text{ or } T_2<T_0) \quad \text{Equation 2}$$

In Equation 1, $T_0$ represents the number of cells before adding the test compound, $T_2$ represents the number of cells after adding the test compound and incubating for 48 hours and C represents the number of cells in the control group with no test compound added after incubating for 48 hours.

The inhibition of cancer cell growth by the test compound (% inhibition) was determined by data regression using the Lotus program from the values calculated according to Equation 1 and the $IC_{50}$ value was calculated from the % inhibition. The result is shown in Table 2.

TABLE 2

| Test compounds | % inhibition for cancer cells | | | | | | |
|---|---|---|---|---|---|---|---|
| | HT1080 | U87-MG | LNCaP | KYSE410 | A 549 | MCF-7 | HepG2 |
| Compound 1 | 62.86 | 48.10 | 34.74 | 62.50 | 94.52 | 94.86 | 87.91 |
| Compound 2 | 87.79 | 86.45 | 84.90 | 88.75 | NT | NT | NT |
| Compound 3 | 87.64 | 89.21 | 92.29 | 92.33 | 75.64 | 85.44 | 67.82 |
| Compound 4 | 75.39 | 56.49 | 73.31 | 56.84 | 94.52 | 95.00 | 89.44 |
| Compound 5 | 67.10 | 45.39 | 62.24 | 48.62 | 94.61 | 95.24 | 89.16 |
| Compound 7 | 88.79 | 89.43 | 49.98 | 86.46 | 93.14 | 94.67 | 98.18 |
| Gleevec | 92.04 | 86.51 | 82.56 | 75.92 | 94.17 | 95.19 | 90.81 |
| Tarceva | 83.07 | 55.96 | 47.12 | 36.30 | NT | NT | NT |
| Iressa | 94.41 | 88.88 | 91.30 | 18.69 | 94.06 | 95.24 | 90.37 |

As described above, since the 6-pyrazolylamido-3-substituted azabicyclo[3.1.0]hexane derivative represented by Formula 1 according to the present invention or a pharmaceutically acceptable salt thereof exhibits superior activity as a T-type calcium channel inhibitor, it can be useful for treating and preventing cerebral diseases, cardiac diseases, cancers and pain-related diseases.

Accordingly, the compound of the present invention is useful for treating and preventing cerebral diseases such as epilepsy, depression, dementia, sleep disorder, diabetes, obesity, etc., cardiac diseases such as hypertension, cardiac dysrhythmia, angina, myocardial infarction, congestive heart failure, etc., cancers such as liver cancer, lung cancer, colon cancer, prostate cancer, breast cancer, uterine cancer, esophageal cancer, brain cancer, etc. and pain-related diseases such as chronic and acute pain, neuropathic pain, etc. since it effectively blocks the T-type calcium channel.

The present invention has been described in detail with reference to specific embodiments thereof. However, it will be appreciated by those skilled in the art that various changes and modifications may be made in these embodiments without departing from the principles and spirit of the invention, the scope of which is defined in the appended claims and their equivalents.

What is claimed is:

1. A compound selected from a group consisting of 6-pyrazolylamido-3-substituted azabicyclo[3.1.0]hexane derivatives represented by Formula 1 and pharmaceutically acceptable salts thereof:

[Formula 1]

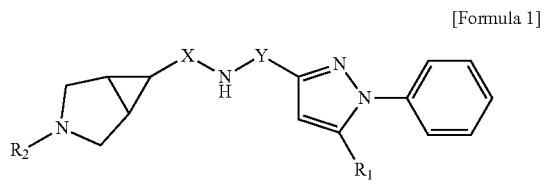

wherein
—X—NH—Y— represents —C(O)NH(CH2)q- or —(CH2)qNHC(O)—;
R1 represents C1-C6 alkyl;
R2 represents C1-C6 alkyl,

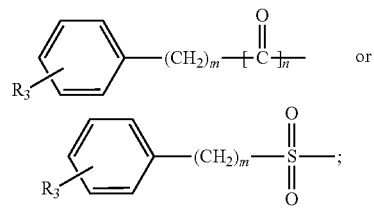

R3 represents hydrogen, C1-C6 alkyl or C1-C6 haloalkyl substituted with 1-6 halogen atom(s); and
each of q, m and n represents an integer from 0 to 6.

2. The compound according to claim 1,
wherein
—X—NH—Y— represents —C(O)NH(CH2)- or —(CH2)NHC(O)—;
R1 represents isobutyl; and
R2 represents methyl, isopropyl, 3-methylbutyl, 3,3-dimethylbutyl, phenyl, 4-(trifluoromethyl)phenyl, benzyl, 4-(trifluoromethyl)benzyl, phenylethyl, 4-(trifluoromethyl)phenylethyl, benzoyl, 2-phenylacetyl, benzenesulfonyl, benzylsulfonyl or phenylethylsulfonyl.

3. A compound selected from:
3-[3-(3,3-dimethylbutyl)-3-azabicyclo[3.1.0]hexane-6-carboxamido]methyl-5-isobutyl-1-phenyl-1H-pyrazole (Compound 1);
3-(3-benzyl-3-azabicyclo[3.1.0]hexane-6-carboxamido)methyl-5-isobutyl-1-phenyl-1H-pyrazole (Compound 2);
5-isobutyl-1-phenyl-3-{3-[4-(trifluoromethyl)phenylethyl]-3-azabicyclo[3.1.0]hexane-6-carboxamido}methyl-1H-pyrazole (Compound 3);
3-(3-benzoyl-3-azabicyclo[3.1.0]hexane-6-carboxamido)methyl-5-isobutyl-1-phenyl-1H-pyrazole (Compound 4);
5-isobutyl-1-phenyl-3-[3-(2-phenylacetyl)-3-azabicyclo[3.1.0]hexane-6-carboxamido]methyl-1H-pyrazole (Compound 5);
5-isobutyl-1-phenyl-3-(3-benzenesulfonyl-3-azabicyclo[3.1.0]hexane-6-carboxamido)methyl-1H-pyrazole (Compound 6);
3-{2-[3-(3,3-dimethylbutyl)-3-azabicyclo[3.1.0]hexane-6-yl]methyl}carbamoyl-5-isobutyl-1-phenyl-1H-pyrazole (Compound 7); or
a pharmaceutically acceptable salt thereof.

4. Pyrazole-azabicyclo[3.1.0]hexane compounds represented by Formula 2 or salt thereof:

[Formula 2]

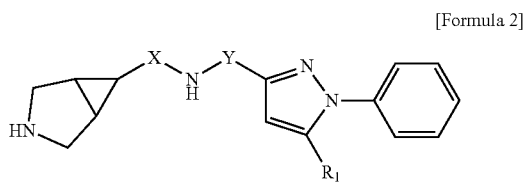

wherein
—X—NH—Y— represents —C(O)NH(CH2)q- or —(CH2)qNHC(O)—;
R1 represents C1-C6 alkyl; and
q represents an integer from 0 to 6.

5. The pharmaceutical composition according to claim 1, which is for treating cerebral diseases selected from epilepsy, depression, dementia, sleep disorder, diabetes or obesity, or for treating cardiac diseases selected from hypertension, cardiac dysrhythmia, angina, myocardial infarction or congestive heart failure, or for treating cancers selected from liver cancer, lung cancer, colon cancer, prostate cancer, breast cancer, uterine cancer, esophageal cancer or brain cancer or for treating pain-related diseases selected from chronic pain, acute pain or neuropathic pain.

6. The pharmaceutical composition comprises the compound according to claim 2 as an active ingredient, which is for treating cerebral diseases selected from epilepsy, depression, dementia, sleep disorder, diabetes or obesity, or for treating cardiac diseases selected from hypertension, cardiac dysrhythmia, angina, myocardial infarction or congestive heart failure, or for treating cancers selected from liver cancer, lung cancer, colon cancer, prostate cancer, breast cancer, uterine cancer, esophageal cancer or brain cancer or for treating pain-related diseases selected from chronic pain, acute pain or neuropathic pain.

7. The pharmaceutical composition comprises the compound according to claim 3 as an active ingredient, which is for treating cerebral diseases selected from epilepsy, depression, dementia, sleep disorder, diabetes or obesity, or for treating cardiac diseases selected from hypertension, cardiac dysrhythmia, angina, myocardial infarction or congestive heart failure, or for treating cancers selected from liver cancer, lung cancer, colon cancer, prostate cancer, breast cancer, uterine cancer, esophageal cancer or brain cancer or for treating pain-related diseases selected from chronic pain, acute pain or neuropathic pain.

* * * * *